United States Patent [19]

Hall et al.

[11] Patent Number: 5,261,822
[45] Date of Patent: Nov. 16, 1993

[54] SURGICAL REFRACTIVE LASER CALIBRATION DEVICE

[75] Inventors: Deborah K. Hall, Menlo Park, Calif.; Erik Rencs; Walter J. Stark, both of Baltimore, Md.

[73] Assignee: Iatrotech, Inc., Del Mar, Calif.

[21] Appl. No.: 3,521

[22] Filed: Jan. 12, 1993

[51] Int. Cl.$^5$ .............................................. G09B 23/28
[52] U.S. Cl. ................................ 434/271; 356/213; 356/121
[58] Field of Search .................. 434/271; 351/221; 356/213, 121

[56] References Cited

U.S. PATENT DOCUMENTS

| | | | |
|---|---|---|---|
| 4,729,655 | 3/1988 | Boggy et al. | 356/121 |
| 4,762,495 | 8/1988 | Maloney et al. | 434/271 |
| 4,762,496 | 8/1988 | Maloney et al. | 434/271 |
| 4,865,551 | 9/1989 | Maloney et al. | 434/271 |
| 4,865,552 | 9/1989 | Maloney et al. | 434/271 |

FOREIGN PATENT DOCUMENTS 187224 8/1987 Japan .................................. 356/121
559126 7/1977 U.S.S.R. ............................. 356/213

OTHER PUBLICATIONS

Langmuir-Blodgett Films, Physics Today Jun,. 1988 pp. 40-46.

*Primary Examiner*—Gene Mancene
*Assistant Examiner*—L. Thomas
*Attorney, Agent, or Firm*—Henri J. A. Charmasson

[57] ABSTRACT

A phantom cornea for calibrating surgical lasers is formed by superimposition of thin-films of alternating colors. After ablation by a laser beam, the resulting spherical cavity appears as a pattern of nested circles whose concentricity and spacing reflect the alignment and intensity of the laser beam. These patterns can be visually or instrumentally analyzed to determine the proper setting of the laser. The calibration cornea can be planar, or arcuate to mimic the natural cornea. The calibration cornea may be mounted in a phantom eyeball including a removable iris of small diameter which constitutes a convenient target for the alignment of the laser beam.

28 Claims, 3 Drawing Sheets

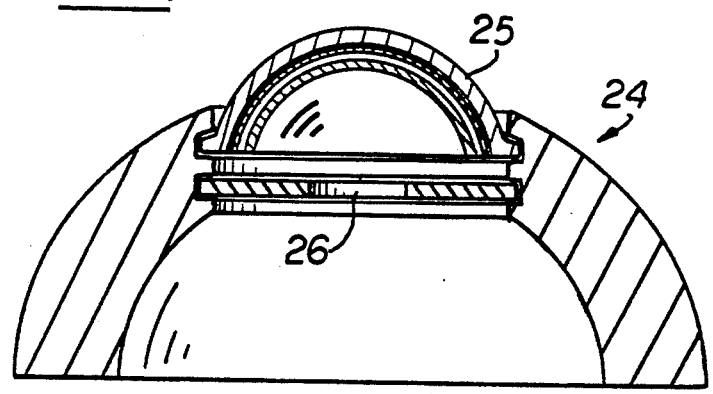

SURGICAL REFRACTIVE LASER CALIBRATION DEVICE

FIELD OF THE INVENTION

This invention relates to laser use in ophthalmic surgery to either diseased tissue from the front of the cornea or to change the curvature of the cornea by tissue removal. More specifically, this invention relates to artificial tissue used to calibrate the intensity of a surgical laser before use on the patient.

BACKGROUND OF THE INVENTION

Prior to this invention, surgical lasers used on corneal tissue were calibrated by first ablating some material on the surface of a polymethyl-methacrylate (PMMA) card. The resulting concave cavity on the surface of the card created a negative-diopter lens. The power of that lens was then measured by means of a lensometer. If the reading differed from a predetermined value, typically −4 diopters, the laser intensity was adjusted by a calibration factor corresponding to the difference between the lensometer reading and the desired surgical power of the laser.

This cumbersome calibration method has two major drawbacks. In the first place, the lensometer provides an approximate reading of the curvature of the ablation. If the ablation was aspheric, wherein the power at the center of the ablation was different than the power at the periphery of it, the lensometer would only give a reading close to the power reading of the central part of the ablation. In the second place, lensometers are not very accurate and exhibit typical errors of up to 6 percent between two readings of the same ablated card.

This prior art calibrating process for surgical laser is not only cumbersome and inaccurate, but also lengthy and ill-adapted to the environment of an operating room.

SUMMARY OF THE INVENTION

The principal and secondary objects of this invention are to provide a convenient and expeditious method for calibrating a laser used to ablate corneal tissue whereby the surgeon can quickly calibrate or recalibrate the laser before and during surgery by visual inspection and/or instrumental measurements. These and other objects are achieved by using a calibration block made of superimposed thin-film layers of polymethyle-methacrylate material. The layers or films have distinctive colors or optical characteristics and their thicknesses are adjusted to create a symmetrical pattern of concentric circles when a spherical cavity is ablated by a laser beam normal to film surfaces. A misalignment of the laser beam results in an eccentricity of the pattern circles. Any deviation from a desired intensity causes a change in the radius of the ablated cavity. This results in changes in the width of the pattern circles which can be detected by visual inspection. Colored and fluorescent doping of the layers can be used to facilitate the detection of variations in the pattern of circles created by the laser ablation.

BRIEF DESCRIPTION OF THE DRAWING

FIG. 7 is a cross-sectional view of a complex ophthalmic phantom.

DESCRIPTION OF THE PREFERRED EMBODIMENT OF THE INVENTION

Figure 1:
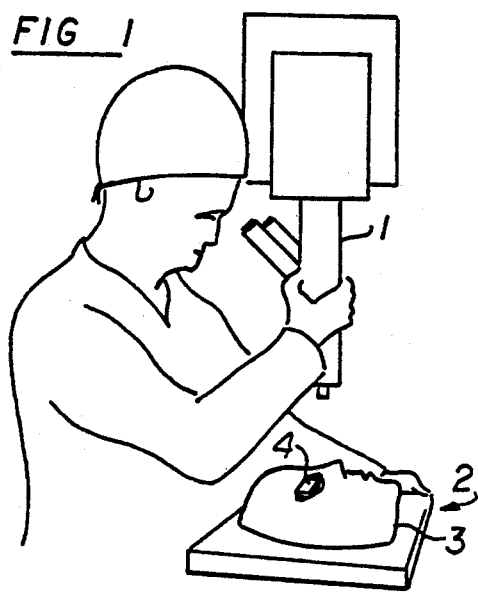
FIG. 1 is an illustration of a surgical laser and calibration block according to the invention.

Referring now to the drawing, there is shown in FIG. 1 a surgical laser 1 being applied to a ophthalmic phantom 2 comprising a simulated human face 3 including a calibration block 4 according to the invention installed in the ocular cavity of the ophthalmic phantom. The laser may be an excimer, solid-state or holmium type such as those commonly used to remove diseased corneal tissue in therapeutic surgery, or to change the curvature of the cornea in corrective surgery. The phantom 2 may be of the type disclosed in U.S. Pat. No. 4,762,495 and U.S. Pat. No. 4,865,551.

Figure 2:
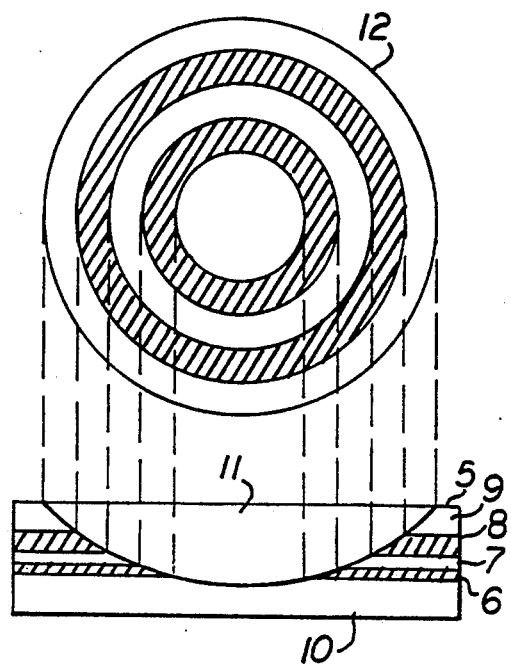
FIG. 2 is a diagram illustrating the formation of the pattern of circles created by the laser ablation on the surface of the calibration block.
Figure 5:
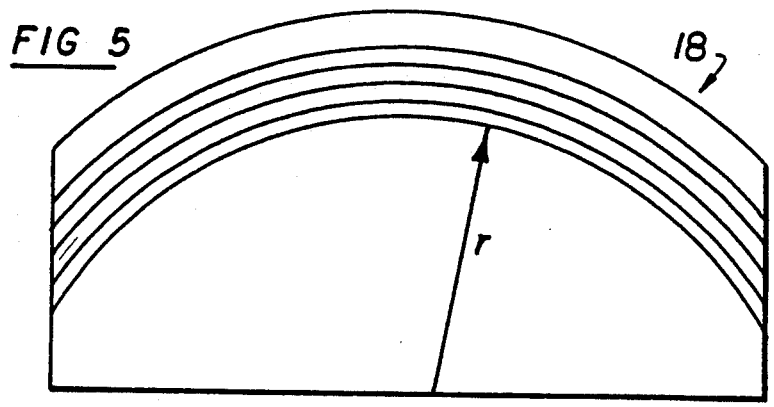
FIG. 5 is a cross-sectional view of an alternate embodiment of the calibration block.

The calibration block may have a planar surface such as the one illustrated in FIG. 2 or may be curved to simulate a human cornea as the one illustrated in FIG. 5.

Figure 4:
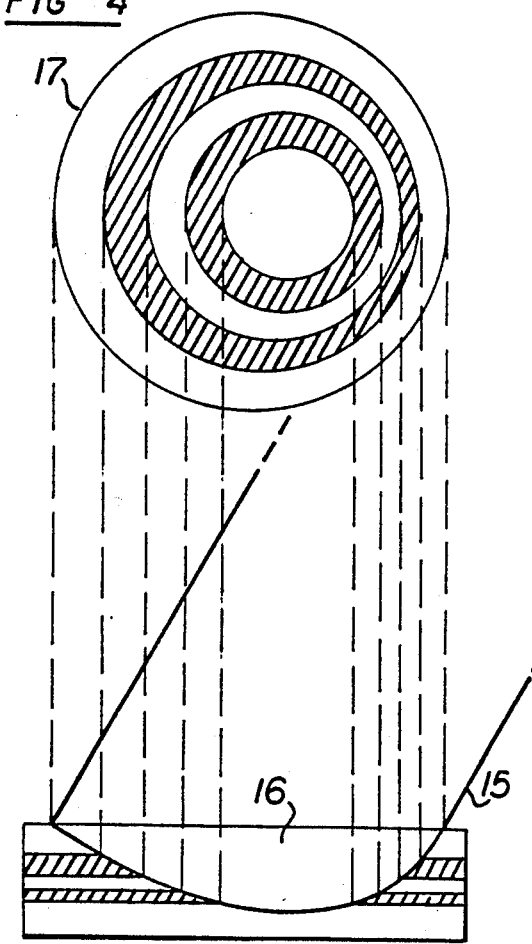
FIG. 4 is a diagram illustrating the eccentricity of the circle pattern due to a misalignment of the laser.
Figure 3:
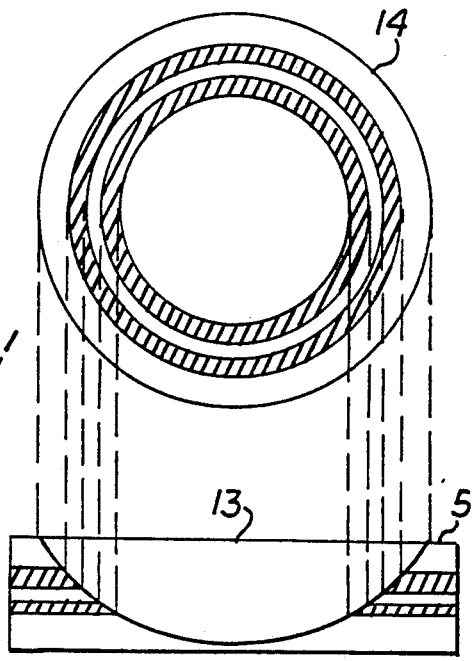
FIG. 3 is a diagram illustrating the variation of circle-width resulting from an increase in the laser intensity.

The calibration block 5 illustrated in FIGS. 2–4 comprises a plurality of thin-films or layers 6, 7, 8 and 9 of polymethyl-methacrylate material over a substrate 10 of the same material. The layers or thin films have thicknesses that increase progressively from the most distal, bottom layer 6 to the top layer 9. The layer thicknesses are adjusted so that when the concave cavity 11 ablated by a laser beam orthogonally striking the surface of the block 5, is viewed from above, it creates a pattern 12 of concentric circles which are evenly spaced from one another. Table 1 lists the series of twelve layer thicknesses calculated to exhibit such a concentric pattern for a cavity corresponding to a lens power of −4 diopters. Such a cavity corresponds to the typical laser intensity required for corneal ablation. Other sets of layer thicknesses may be calculated according to the following formula:

$$t_{(i)} = \sqrt{R^2 - \left[(N-i)\frac{R}{N}\right]^2} - \sum_{j=0}^{j=i-1} t_j$$

wherein $R = \frac{0.36}{P} \cdot 1000$

P is the dioptric power of the cavity-formed lens.
t is the thickness of each layer.
N is the number of layers over a full quadrant.
i is the layer ranking.

TABLE I

| POWER −4 Layer | | RADIUS 90 M Thickness (micron) |
|---|---|---|
| Bottom | 1 | 0.347 |
| | 2 | 1.042 |
| | 3 | 1.736 |
| | 4 | 2.736 |
| | 5 | 3.125 |
| | 6 | 3.82 |

TABLE I-continued

| POWER −4 Layer | RADIUS 90 M Thickness (micron) |
| --- | --- |
| 7 | 4.515 |
| 8 | 5.209 |
| 9 | 5.904 |
| 10 | 6.6 |
| 11 | 7.245 |
| Top 12 | 7.99 |

FIG. 2 illustrates the cavity 13 formed by a laser beam of greater intensity that yields a corresponding lens of a greater negative power. It should be noted that the corresponding top plan view pattern 14 has circles with asymmetrical spacing. Accordingly, the improper setting of the laser intensity can be quickly detected by visual inspection of the circle pattern.

In the illustration of FIG. 4, the block 5 is ablated by a misaligned, i.e. oblique laser beam 15. The misalignment is purposely exaggerated in the illustration for the sake of clarity. The floor of the resulting cavity 16 is aspheric, resulting in a pattern 17 of eccentric circles.

The visual or instrumental inspection of the circle pattern can be facilitated by giving the layers different optical properties. For instance, each layer may be doped with a hue different from the hue used to dope any other contiguous layer. Alternately, every other layer may be doped with fluorescin or ammonia in order to create a luminescent glow under light. The refractive or other physical properties of the layers may be varied by using the same or different material with distinct molecular weights.

The layers or thin films can be formed over the substrate according to methods well-known in the art of integrated circuit fabrication such as epitaxial growth or vapor deposition. A near-molecular thickness of film can be achieved by organic deposition of Langmuir-Blodgett films. Other processes such as spin-coating and flame-spraying may be used to build the block layers.

In the calibrating block illustrated in FIG. 5, the layers are built upon a substrate having a convex spherical surface with a radius of approximately 1 centimeter corresponding to the radius of a human cornea.

As in the first embodiment, the layer thicknesses can be calculated to yield a concentric and symmetrical top plan-view pattern according to the following formula:

$$r(i) = \sqrt{\left(\frac{iR}{N}\right)^2 + \left[r^2 - \sqrt{R^2 - \left(\frac{iR}{N}\right)^2}\right]^2} - (r - R) - \sum_{j=o}^{j=i=1} tj$$

wherein r is the calibration block radius.

Figure 6:
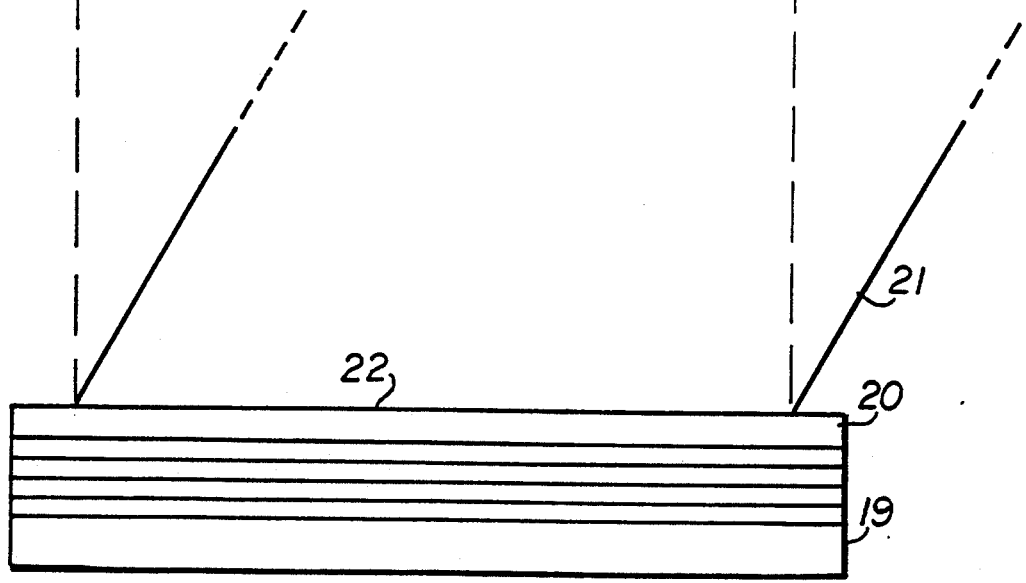
FIG. 6 illustrates a fluorescent pattern resulting from a misalignment of the laser.

In the calibration block 19 illustrated in FIG. 6, the top layer 20 is doped with fluorescin, ammonia or another luminescent compound. When a laser beam 21 impinges upon the top surface of the upper layer 20 it creates a luminescent spot 22. If the laser beam is oblique rather than normal, as illustrated, the luminescent spot assumes an ovoidal shape 23 rather than a perfect circular shape. The procedure can thus be used to accurately position the laser to a normal position through visual observation of the luminescent spot 22.

Although PMMA has been used in connection with the above-described embodiments of the calibration block, other synthetic or natural materials that substantially mimic the properties of the natural cornea, such as collagen, may be used as base material.

FIG. 7 illustrates a ophthalmic phantom 24 of the type disclosed in U.S. Pat. Nos. 4,762,496 and 4,865,551 which can be mounted in the facial cast 2 of FIG. 1.

The phantom eye 24 is characterized by the movable, multilayered cornea 25, and a removable iris 26 installed behind it. The cornea may be formed according to the above-described techniques to produce the symmetrical ring pattern upon laser ablation.

The removable iris 26 with a pupil diameter of approximately 2 millimeters provides a convenient target when centering the laser beam. After ablation, the iris can be removed, and the shape of the ablation can be measured with a lensometer without having to dismount the phantom cornea.

The iris 26 is preferably made in a dark color for better contrast with the fluorescent zones of the cornea.

Every other layer of the cornea, or the entire cornea in some applications, should be black in order to allow better reflection and facilitate cornea topography.

While the preferred embodiments of the invention have been described, modifications can be made and other embodiments may be devised without departing from the spirit of the invention and the scope of the appended claims.

What is claimed is:

1. The combination of a surgical laser and an artificial optical body for testing and calibrating the intensity of said surgical laser wherein said optical body comprises:
   a plurality of superimposed, parallel layers of a material ablatable by said surgical laser and having substantially the same effect as a human cornea would have when ablated by a surgical laser, said layers having distinctive optical properties wherein any one of said layers has a different optical characteristic and a different thickness than any other layer contiguous to said one of said layers whereby more than one of said layers are ablatable by said surgical laser.

2. The combination of claim 1, wherein said material is selected from a group consisting of polymethylmethacrylate and collagen.

3. The combination of claim 1, wherein said layers have progressively varying thicknesses.

4. The combination of claim 1, wherein at least one of said layers is doped with a fluorescent compound.

5. The combination of claim 3, wherein the thickness of each of said layers is selected to create a pattern of concentric rings having alternate optical characteristics and equal plan view width when said body is laser-ablated along an axis normal to said layers to form a concave surface corresponding to a lens of a given diopter power.

6. The combination of a surgical laser and an artificial optical body for testing and calibrating the intensity of said surgical laser wherein said optical body comprises:
   a plurality of superimposed, parallel layers of synthetic material including a distal bottom layer and a proximal surface layer, said layers having distinctive optical properties wherein any particular layer has a different optical characteristic than any other layer contiguous to said particular layer;

wherein said layers are planar, and wherein said layers have thicknesses increasing progressively from said bottom layer to said surface layer.

7. The combination of claim 6, wherein any particular layer has a different color than any other layer contiguous to said particular layer.

8. The combination of claim 6, wherein any particular layer has a different molecular weight than any other layer contiguous to said particular layer.

9. The combination of claim 6, wherein at least one of said layers is doped with a fluorescent compound.

10. The combination of claim 6, wherein said layers are made of polymethyl-methacrylate.

11. The combination of claim 6, wherein said layers comprise a plurality of epitaxially-grown thin films.

12. The combination of claim 6, wherein said layers comprise a plurality of vapor-deposited thin films.

13. The combination of claim 6, wherein said layers comprise a multi-layer Langmuir-Blodgett film.

14. The combination of claim 6, wherein said layers comprise a plurality of spin-coated films.

15. The combination of a surgical laser and an artificial optical body for testing and calibrating the intensity of said surgical laser wherein said optical body comprises:
a plurality of superimposed, parallel layers of synthetic material including a distal bottom layer and a proximal surface layer, said layers having distinctive optical properties wherein any particular layer has a different optical characteristic than any other layer contiguous to said particular layer;
wherein said layers are convexly arcuate, and are shaped and dimensioned to simulate a human cornea; and
wherein said layers have thicknesses increasing progressively from said bottom layer to said surface layer.

16. The combination of claim 15, wherein any particular layer has a different color than any other layer contiguous to said particular layer.

17. The combination of claim 15, wherein any particular layer has a different molecular weight than any other layer contiguous to said particular layer.

18. The combination of claim 15, wherein at least one of said layers is doped with a fluorescent compound.

19. The combination of claim 15, wherein said layers are made of polymethyl-methacrylate.

20. The combination of claim 15, wherein said layers comprise a plurality of epitaxially-grown thin films.

21. The combination of claim 15, wherein said layers comprise a plurality of vapor-deposited thin films.

22. The combination of claim 15, wherein said layers comprise a multi-layer Langmuir-Blodgett films.

23. The combination of claim 15, wherein said layers comprise a plurality of spin-coated films.

24. The combination of a surgical laser and an artificial optical body for testing and calibrating the intensity of said surgical laser wherein said optical body comprises:
a plurality of superimposed, parallel planar layers of synthetic material including a distal bottom layer and a proximal surface layer, said layers having distinctive optical properties wherein any particular layer has a different optical characteristic than any other layer contiguous to said particular layer;
wherein the thickness ti of each of said layers having a rank i from said bottom layer having a rank i=1 to said surface layer having a rank i=N is adjusted to create a pattern of concentric rings having alternate optical characteristics and equal plan view width when said body is laser-ablated along an axis normal to said layers to form a concave surface corresponding to a lens of a given diopter power P, where N is the total number of said layers.

25. The combination of claim 24, wherein the thicknesses t(i) of each of said layers is equal to $$\sqrt{R^2 - \left[(N-i)\frac{R}{N}\right]^2} - \sum_{j=o}^{j=i-1} t_j$$

wherein $R = \frac{0.36}{P} 1000$.

26. The combination of a surgical laser and an artificial optical body for testing and calibrating the intensity of said surgical laser wherein said optical body comprises:
a plurality of superimposed, parallel planar layers of synthetic material including a distal bottom layer and a proximal surface layer, said layers having distinctive optical properties wherein any particular layer has a different optical characteristic than any other layer contiguous to said particular layer;
wherein the thickness ti of each of said layers having a rank i from said bottom layer having a rank i=1 to said surface layer having a rank i=N is adjusted to create a pattern of concentric rings having alternate optical characteristics and equal plan view width when said body is laser-ablated along an axis normal to said layers to form a concave surface corresponding to a lens of a given diopter power P, where N is the total number of said layers.

27. The combination of claim 26, wherein said body is shaped and dimensioned to simulate a human cornea; and said combination further comprises:
a phantom eyeball having a central cavity closed at a proximal end by said body; and
an artificial iris mounted within said cavity behind said body.

28. The combination of claim 26, wherein the thicknesses t(i) of each of said layers is equal to $$\sqrt{R^2 - \left[(N-i)\frac{R}{N}\right]^2} - \sum_{j=o}^{j=i-1} t_j$$

wherein $R = \frac{0.36}{P} 1000$.

* * * * *

UNITED STATES PATENT AND TRADEMARK OFFICE
CERTIFICATE OF CORRECTION

PATENT NO. : 5,261,822
DATED : November 16, 1993
INVENTOR(S) : Deborah K. Hall, et al It is certified that error appears in the above-indentified patent and that said Letters Patent is hereby corrected as shown below:

Column 6, line 29, replace "planar" with --convexly arcuate--.

Signed and Sealed this

Eighteenth Day of October, 1994

Attest:

BRUCE LEHMAN

*Attesting Officer*     *Commissioner of Patents and Trademarks*